(12) United States Patent
Lawrence et al.

(10) Patent No.: US 8,519,713 B2
(45) Date of Patent: Aug. 27, 2013

(54) SYSTEM AND METHOD FOR QUALITATIVE AND QUANTITATIVE ANALYSIS OF GASEOUS COMPONENTS OF MULTIPHASE HYDROCARBON MIXTURES

(75) Inventors: Jimmy Lawrence, Amherst, MA (US); Nathan Lawrence, Huntingdon (GB); Kay Robinson, Milton (GB)

(73) Assignee: Schlumberger Technology Texas, Sugar Land, TX (US)

( * ) Notice: Subject to any disclaimer, the term of this patent is extended or adjusted under 35 U.S.C. 154(b) by 482 days.

(21) Appl. No.: 12/516,260

(22) PCT Filed: Sep. 21, 2007

(86) PCT No.: PCT/GB2007/003572
§ 371 (c)(1),
(2), (4) Date: Feb. 24, 2010

(87) PCT Pub. No.: WO2008/065324
PCT Pub. Date: Jun. 5, 2008

(65) Prior Publication Data
US 2010/0148780 A1    Jun. 17, 2010

(30) Foreign Application Priority Data
Dec. 2, 2006 (GB) ................................. 0624108.7

(51) Int. Cl.
*G01V 3/18* (2006.01)
(52) U.S. Cl.
USPC ....................................................... 324/324
(58) Field of Classification Search
USPC .............. 324/324; 204/193, 194, 400–435, 204/227–286.1; 205/775, 786.5, 793; 436/120, 436/121
See application file for complete search history.

(56) References Cited

U.S. PATENT DOCUMENTS

| | | | | |
|---|---|---|---|---|
| 3,915,831 A | * | 10/1975 | Riseman et al. | 204/419 |
| 5,656,827 A | * | 8/1997 | Kang et al. | 257/76 |
| 5,746,900 A | * | 5/1998 | Venkatasetty | 204/415 |
| 6,939,717 B2 | | 9/2005 | Jiang et al. | |
| 6,995,360 B2 | | 2/2006 | Jones et al. | |

(Continued)

FOREIGN PATENT DOCUMENTS

| | | |
|---|---|---|
| GB | 2391314 A | 2/2004 |
| GB | 2397651 A | 7/2004 |

(Continued)

OTHER PUBLICATIONS

Batina et al: "Determination of elemental sulphur, sulphide and their mixtures in electrolyte solutions by a.c. voltammetry", Analytica Chimica Acta, vol. 267, 1992, pp. 157-164.

(Continued)

*Primary Examiner* — Melissa Koval
*Assistant Examiner* — Daniel Miller
(74) *Attorney, Agent, or Firm* — Rachel Greene; Jakulo Michna; Brigit Laftey

(57) ABSTRACT

Embodiments of the present invention provide systems and methods for detection and/or measurement of gaseous components of multiphase mixtures containing one or more hydrocarbons that may be retrieved down a wellbore or may be being transported in a pipeline. More specifically, but not by way of limitation, embodiments of the present invention may provide for separation of the gaseous components from the multiphase mixtures and detection and/or measurement of the separated gaseous components by direct oxidation or reduction.

12 Claims, 5 Drawing Sheets

(56) References Cited

U.S. PATENT DOCUMENTS

| | | | |
|---|---|---|---|
| 7,025,138 B2* | 4/2006 | Kurkjian et al. | 166/250.05 |
| 2002/0121370 A1 | 9/2002 | Kurkjian et al. | |
| 2003/0134426 A1 | 7/2003 | Jiang et al. | |
| 2003/0206026 A1 | 11/2003 | Diakonov et al. | |
| 2004/0045350 A1 | 3/2004 | Jones et al. | |
| 2005/0029125 A1* | 2/2005 | Jiang et al. | 205/775 |
| 2005/0140368 A1* | 6/2005 | Freedman | 324/303 |
| 2005/0242807 A1* | 11/2005 | Freedman | 324/303 |
| 2005/0259499 A1 | 11/2005 | Kim et al. | |
| 2006/0243603 A1 | 11/2006 | Jiang et al. | |
| 2011/0168446 A1* | 7/2011 | Lemenager et al. | 175/50 |

FOREIGN PATENT DOCUMENTS

| | | | |
|---|---|---|---|
| GB | 2402476 A | | 12/2004 |
| WO | WO2001063094 A1 | | 8/2001 |
| WO | WO2004011929 A1 | | 2/2004 |
| WO | WO 2004/063743 | * | 7/2004 |
| WO | WO2005066618 A1 | | 7/2005 |
| WO | WO2005121779 A1 | | 12/2005 |
| WO | WO 2006/067491 | * | 6/2006 |

OTHER PUBLICATIONS

Garcia-Calzada et al.: "Potentiometric determination of sulphur in solid samples with a sulphide selective electrode", Analytica Chimica Acta, vol. 380, 1999, p. 39-45.

Jeroschewski et al.: "Galvanic sensor for the determination of hydrogen sulphide/sulphide in aqueous media", Fresenius' Journal of Analytical Chemistry, vol. 346, 1993, pp. 930-933.

Jeroschewski et al.: "Galvanic sensor for determination of hydrogen sulfide", Electroanalysis, vol. 6, 1994, pp. 769-772.

Jeroschewski et al.: "A flow analysis system with an amperometric detector for the determination of hydrogen sulphide in waters", Fresenius' Journal of Analytical Chemistry, vol. 354, 1996, pp. 169-172.

Jeroschewski et al: "An amperometric microsensor for the determination of H2S in aquatic environments", Analytical Chemistry, vol. 68, 1996, pp. 4351-4357.

Kohl et al.: "A H2S microsensor for profiling biofilms and sediments: application in an acidic lake sediment", Aquatic Microbial Ecolology, vol. 15, 1998, pp. 201-209.

Lawrence et al.: "Analytical strategies for the detection of sulfide: a review", Talanta, vol. 52, 2000, pp. 771-784.

Lawrence et al.: "The electrochemical analog of the methylene blue reaction: a novel amperometric approach to the detection of hydrogen sulfide", Electroanalysis, vol. 12, 2000, pp. 1453-1460.

Lawrence et al.: "A thin-layer amperometric sensor for hydrogen sulfide: The use of microelectrodes to achieve a membrane-independent response for Clark-type sensors", Analytical Chemistry, vol. 75, 2003, pp. 2499-2503.

Lawrence et al.: "Voltammetric characterization of a N,N'-diphenyl-p-phenylenediamine-loaded screen-printed electrode: a disposable sensor for hydrogen sulfide", Analytical Chemistry, vol. 75, 2003, pp. 2054-2059.

Lawrence et al.: "Amperometric detection of sulfide at a boron doped diamond electrode: the electrocatalytic reaction of sulfide with ferricyanide in aqueous solution", Electroanalysis, vol. 14, 2002, pp. 499-504.

Lawrence et al.: "Electrochemical determination of hydrogen sulfide at carbon nanotube modified electrodes", Analytica Chimica Acta, vol. 517, 2004, pp. 131-137.

Schiavon et al: "Electrochemical detection of trace hydrogen sulfide in gaseous samples by porous silver electrodes supported on ion-exchange membranes (solid polymer electrolytes)", Analytical Chemistry, vol. 67, 1995, pp. 31 8-323.

Stanic et al.: "Determination of sulfur compounds in the sol-gel processing of GeS2 by potentiometric titration", Electrochimica Acta, vol. 43, 1998, pp. 2639-2647.

Combined Search and Examination Report of British Patent Application Serial No. GB0624108.7 dated Apr. 27, 2007.

International Search report and Written Opinion of PCT Application No. PCT/GB2007/003572 dated Dec. 28, 2007.

* cited by examiner

SYSTEM AND METHOD FOR QUALITATIVE AND QUANTITATIVE ANALYSIS OF GASEOUS COMPONENTS OF MULTIPHASE HYDROCARBON MIXTURES

BACKGROUND OF THE INVENTION

Analysis of fluid samples associated with wellbores penetrating earth formations for hydrocarbon recovery may comprise collecting and analyzing samples from the wellbore or from an earth formation(s) surrounding the wellbore. In addition, it is often necessary to analyse and evaluate hydrocarbon mixtures flowing from such wellbores in pipelines and the like and hydrocarbon mixtures found in and around such wellbores during well servicing and the like. For example, the analysis of fluid samples from a hydrocarbon well for the determination of phase behaviour and chemical composition may be an important step in the evaluation of the producibility and economic value of the hydrocarbon reserves in the earth formation. An important factor in determining the economic value of gas and liquid hydrocarbon reserves is their chemical composition, particularly the concentration of gaseous components, such as hydrogen sulphide, carbon dioxide, hydrogen, sulphide and lighter hydrocarbons (such as propane, ethane, methane or the like). Additionally, corrosion of transportation pipelines and analysis of well servicing actions are also important in the development and production of hydrocarbons from the wellbore. Therefore, real time gas detection is an important process for downhole fluid analysis, hydrocarbon transportation and well servicing.

Contrary to surface analysis, various available approaches—optical, chromatography, etc—to detect gaseous components—such as hydrogen sulphide, carbon dioxide, hydrogen, mercapto gases and methane—present in downhole environments have been difficult to commoditize due to limitations such as the downhole operating environment, which may involve high temperatures and/or pressures, size of the downhole tools for making such measurements and the presence of water and/or other fluids.

In the case of hydrogen sulphide ("$H_2S$"), its presence in fluids found in the permeable formations of oil wells has an important impact on the economic value of the produced hydrocarbons and production operations. Typically, the sulfur content of crude oils is in the range 0.3-0.8 weight percent and the $H_2S$ content of natural gas is in the range 0.01-0.4 weight percent, although concentrations of $H_2S$ in natural gas of up to 30 weight percent have been reported. Several reports have claimed a systematic increase in the sulphur content of crude oils over the past 10-20 years and anticipate further significant increases in the concentration of $H_2S$ in both oil and natural gas.

Together with carbon dioxide ("$CO_2$"), the presence of $H_2S$ in downhole fluids may give rise to safety and logistical problems. For example, the leading causes of mechanical failure of materials in the oil and gas industry are estimated as follows: $CO_2$ corrosion (28%), $H_2S$ stress cracking (18%), welding (18%), pitting (15%), erosion (12%), galvanic (6%) and stress (3%). As such, for downhole tools, equipment or the like, corrosion caused by gaseous elements and associated problems may be reduced/managed by measuring/detecting such gaseous components.

However, surface measurement/detection of such gas components is problematic because, among other things, transporting the sample to the surface for analysis is inefficient as it is time consuming, and as a result costly, and the transportation process may affect accurate measurement/detection due to the change in environment. With regard to $H_2S$, a problem associated with sampling fluids containing $H_2S$ is partial loss of the $H_2S$ due to reaction of the $H_2S$ with metal components, particularly those made from iron-based metals. $H_2S$ readily forms non-volatile and insoluble metal sulphides by reaction with many metals and metal oxides, and this prevents accurate analysis of $H_2S$ in a fluid sample transported to the surface in a metallic tool. Since fluid samples are usually collected in metal containers, which are able to maintain the pressures at which the samples were collected, a problem associated with sampling fluids containing $H_2S$ is partial loss of the gas by reaction of the $H_2S$ with the metal components, particularly those made from iron-based metals. After contact of the $H_2S$ with metal components during transport, any measurements performed at the surface may give an underestimation of the true $H_2S$ content.

With regard to downhole detection and/or measurement of gaseous components of downhole fluids various problems exist. For example, it may be difficult to determine properties of the gaseous components directly from the fluid sample. Additionally, the high temperatures and pressures in the wellbore may make use of chemical reactions or the like problematic.

SUMMARY OF THE INVENTION

Embodiments of the present invention provide systems and methods for detection and/or measurement of gaseous components of multiphase mixtures containing one or more hydrocarbons. More specifically, but not by way of limitation, embodiments of the present invention provide for separation of gaseous components from downhole fluids and/or multiphase mixtures containing one or more hydrocarbons and detection and/or measurement of the separated gaseous components by direct oxidation or reduction.

In one embodiment of the present invention, a gas sensor for detecting or measuring a gas component of a multiphase mixture containing one or more hydrocarbons is provided, the gas sensor comprising, a sensing volume, a nonsolid conductive material disposed within the sensing volume, a sensing surface in gaseous communication with the sensing volume, a plurality of electrodes disposed within the sensing volume coupled with a potential source and configured to provide a potential sweep across the nonsolid conductive material, wherein one of the plurality of electrodes comprises a working electrode, and wherein composition of the working electrode is selected to provide for detection or measurement of a specific gas in the multiphase mixture, and a device for measuring a current flowing through the nonsolid conductive material.

In another embodiment of the present invention, a wellbore tool configured with a sampling probe and sampling conduit may be deployed down a wellbore, The sampling probe may be used to collect a fluid sample from the wellbore of from the a surrounding formation. The fluids may be drawn into the wellbore tool and into a collection volume from which a gaseous component of the collected fluid sample may enter a sensing volume through a gas permeable membrane, the membrane preventing fluids in the fluid sample entering the sensing volume. The sensing volume may contain a nonsolid conducting material into which the gas component passing through the gas permeable membrane may flow. In the sensing volume, a plurality of electrodes may be configured to apply a potential difference across the nonsolid conducting material and to provide for direct oxidization or reduction of the gaseous component in the sensing volume. Configuring the electrodes to provide for direct oxidation or reduction may comprise determining the make up of a reference electrode to provide for the direct oxidation or reduction of a selected gaseous component. From measurement and/or processing of an oxidation or reduction current associated with the direct oxidization, the gaseous component may be detected/measured.

In certain aspects, a counter electrode, a reference electrode and a working electrode may be used. In other aspects, a guard electrode may also be used to scavenge interfering gases. In some embodiments of the present invention, the reference electrode may comprise a silver-silver chloride electrode, a saturated calomel electrode or the like.

For detection of $H_2S$, a boron doped diamond or glassy carbon working electrode may be used as the working electrode. In other aspects for detection of $H_2S$, an edge plane pyrolitic graphite ("EPPG") electrode, carbon nanotubes, n-doped nanotubes or p-doped nanotubes may be used as the working electrode. In yet other aspects, platinum electrodes may be used to provide for detection/measurement of lighter hydrocarbons or hydrogen. In further aspects, gold electrodes may be used to provide for detection/measurement of sulphide. And in still other aspects, palladium electrodes may be used to provide for detection/measurement of lighter hydrocarbons and/or hydrogen.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

The invention will be better understood in the light of the following description of non-limiting and illustrative embodiments, given with reference to the accompanying drawings, in which.

DETAILED DESCRIPTION OF THE INVENTION

Embodiments of the present invention provide systems and methods for downhole detection and/or measurement of gaseous components of samples of fluid mixtures retrieved from a wellbore penetrating an earth formation. More specifically, but not by way of limitation, embodiments of the present invention provide for separation of a gaseous component from the fluid samples collected in the wellbore and detection and/or measurement of the separated gaseous components by direct oxidation. The fluid samples may be collected from the wellbore or from the earth formation surrounding the wellbore.

Figure 1A:
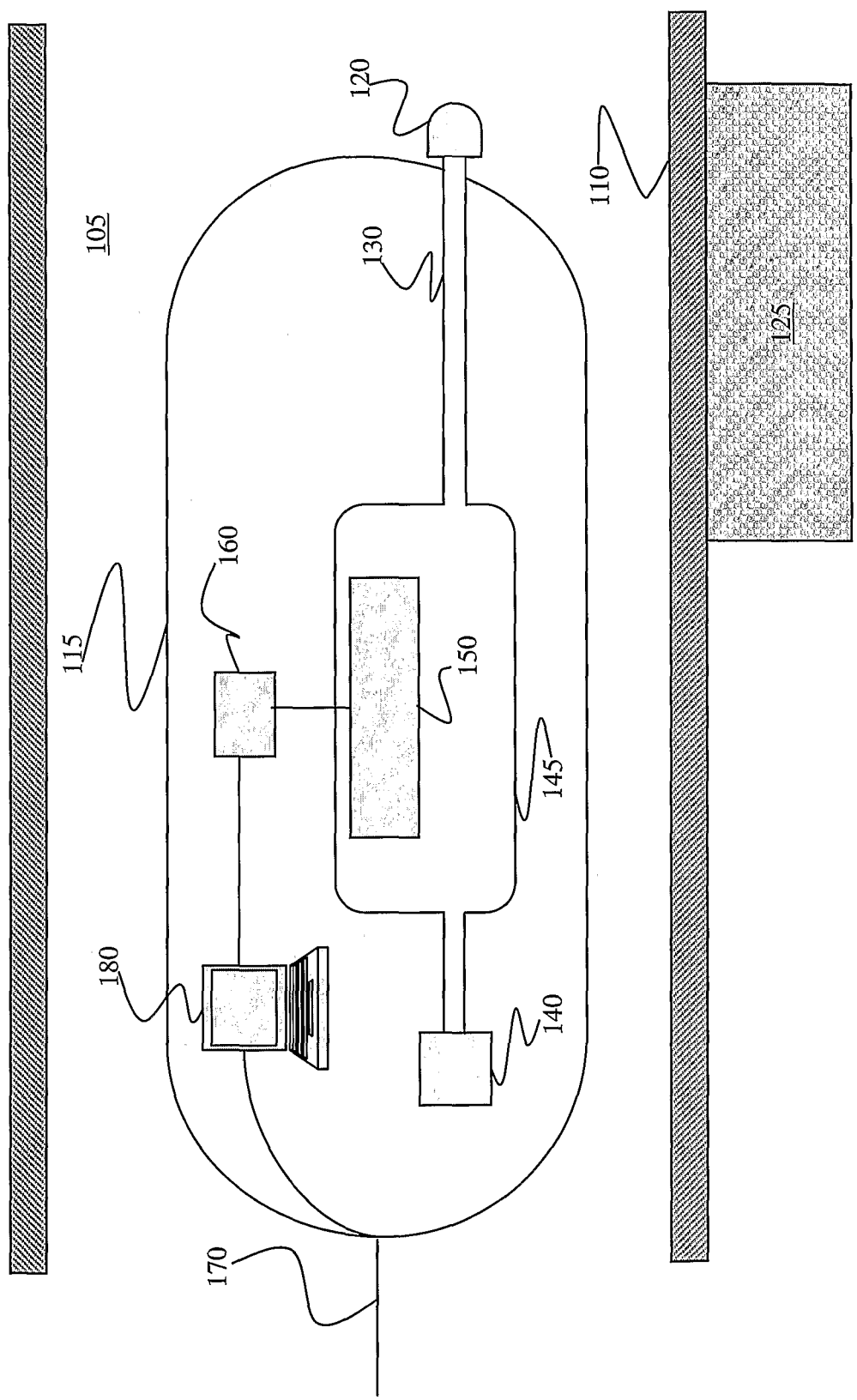
FIG. 1A provides a schematic-type illustration of a system for detecting/measuring gaseous components of downhole fluids in a wellbore, in accordance with an embodiment of the present invention.

FIG. 1 provides a schematic-type representation of a system for detecting/measuring gaseous components of downhole fluids in a wellbore, in accordance with an embodiment of the present invention. In an embodiment of the present invention, a wellbore tool 115 may be positioned in and/or lowered into a wellbore 105. Merely by way of example, the wellbore tool 115 may comprise an elongated substantially cylindrical body that may suspended on a wireline (not shown) in the wellbore 105; where the wireline may provide for moving the wellbore tool 115 in the wellbore 105 to different sampling locations.

A sampling probe 120 may be coupled with the wellbore tool 115 to provide for sampling one or more fluids associated with the wellbore 105. In certain aspects, the wellbore tool 115 may be positioned in the wellbore 105 adjacent to an earth formation 125 to be investigated. In such aspects, the sampling probe 120 may be urged into contact with the earth formation 125. Control of the sampling probe 120 may be provided by hydraulically operated rams (not shown) or the like. The hydraulically operated rams or other means for manoeuvring the wellbore tool 115 may provide for moving the wellbore tool 115 in the wellbore 105. For example, the hydraulically operated rams may project radially from the wellbore tool 115 on the opposite side of the wellbore tool 115 from the sampling probe 120. In this way the hydraulically operated rams may come into contact with a sidewall 110 of the wellbore 105 and push the wellbore tool 115 laterally in the wellbore 105 causing the sampling probe 120 on the other side of the wellbore tool 115 to come into contact with the sidewall 110; the sampling probe 120 coming into contact with a portion of the sidewall 110 that is on the opposite side of the wellbore 105 to the section of the sidewall 110 contacted by the hydraulically operated rams. While, the preceding discloses use of the present system to sample formation fluids, other embodiments of the present invention may provide for sampling fluids/mixtures in the wellbore 105.

The sampling probe 120 may be coupled with a sampling conduit 130 to provide for a flow of any sampled fluids/mixtures into the wellbore tool 115. The sampling conduit 130 may be coupled with a pump 140 or the like. The pump 140 or the like may be used to draw a sample of a fluid/mixture through the sampling probe 120 into a sample chamber 145. The pump 140 may be controlled from a surface location that may be proximal to the top of wellbore 105 and this control may be performed via a wireline 170 or the like coupled with the wellbore tool 115 and control circuitry (not shown) within the wellbore tool 115. It will be appreciated that this control circuitry may include valves (not shown) for selectively routing the sampled fluids/mixtures to the sample chamber 145 to a dump outlet (not shown) or the like, but these have been omitted for the sake of simplicity. The control circuitry may also be used to control the flow of the sampled fluids/mixtures, to route an amount of the fluids/mixtures to the sample chamber 145 and/or the like. A processor (not shown) may be coupled with the control circuitry to aid in the sampling of the fluids/mixtures.

In accordance with an embodiment of the present invention, an electrochemical sensor 150 may be positioned in the sample chamber 145. The electrochemical sensor 150 may be located so as to come into contact with the fluids/mixtures in the sample chamber 145 and may produce an output current that is dependent on an amount of one or more gaseous components in the sampled fluid/mixture. In an embodiment of the present invention the electrochemical sensor 150 may comprise a plurality of electrodes and a potential source for applying a potential difference across the plurality of electrodes and configured so as to directly oxidize or reduce one or more gaseous components contacting the plurality of the electrodes. The oxidation and or reduction of the one or more gaseous components by the electrochemical sensor 150 results in the production of an oxidization or reduction current. The oxidation or reduction current may be measured by a current measurement device 160, which may be a digital ammeter, a digital current measuring circuit, a potentiostat, a galvanostat and/or the like.

In some embodiments of the present invention a processor 170, which may be a software program or the like, may process the output from the current measurement device 160 to provide for detection of the oxidation current and transmitting of data concerning the oxidation current to the surface via the wireline 170. The processor 180 may be configured to process values of the output current from the electrochemical sensor 150 to determine the onset of the oxidation current, an amount of the gaseous component that may correspond to the value of the oxidation current and/or the like. The processor 180 may also be coupled with the electrochemical sensor 150, the control circuitry, and/or the like to provide for control of the sampling, control of the sensing and/or the like. Merely by way of example, in some aspects, the processor 180 may control potential differences applied to the electrodes comprising the electrochemical sensor 150 and vary these potential differences during the sampling/analyzing process.

Figure 1B:
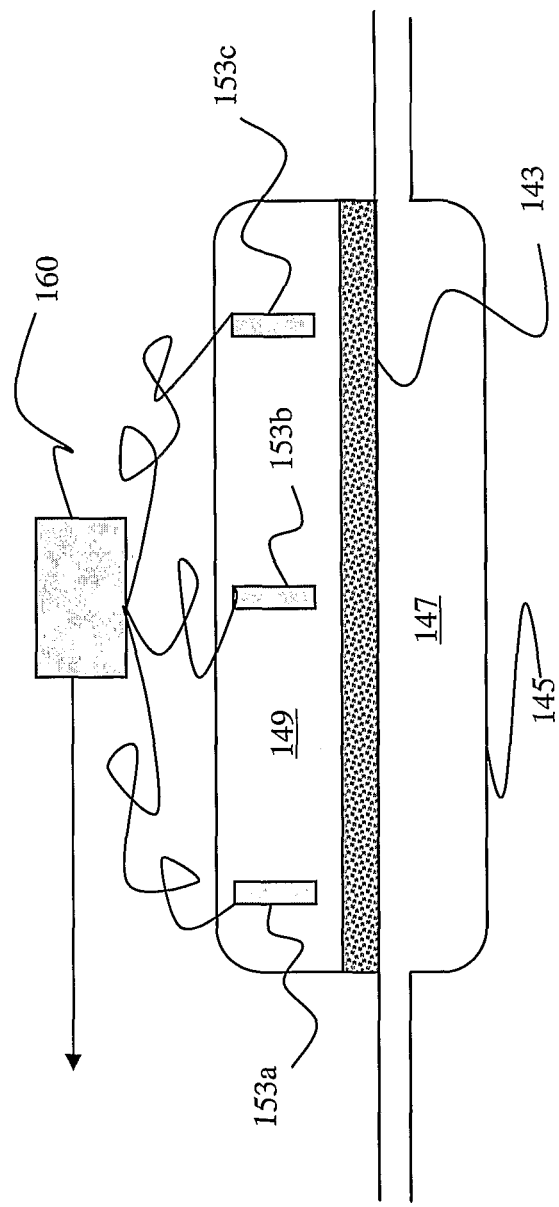
FIG. 1B provides an expanded view of the sample chamber 145 and electrochemical sensor 150 in a system for detecting/measuring gaseous components of downhole fluids in a wellbore, in accordance with an embodiment of the present invention.

FIG. 1B provides an expanded view of the sample chamber 145 and electrochemical sensor 150, in accordance with an embodiment of the present invention. In certain embodiments of the present invention, the sample chamber 145 may be coupled with a gas permeable membrane 143. The gas permeable membrane 143 may be configured to provide that two volumes—a sample volume 147 and a detection/analysis volume 149—are in gaseous communication with one another via at least a portion of the gas permeable membrane 143. A sample of the fluid/mixture flowing into the wellbore tool 115 may flow into the sample volume 147. Gaseous components in the fluid/mixture in the sample volume 147 may pass through the gas permeable membrane 143 into the detection/analysis volume 149.

The detection/analysis volume 149 may contain a nonsolid conducting material. In certain embodiments of the present invention, the electrochemical sensor 150 may comprise three electrodes, the three electrodes providing contact with the nonsolid conducting material. In other embodiments of the present invention, the electrochemical sensor 150 may comprise different pluralities of electrodes. The composition of the nonsolid conducting material and/or the different electrodes comprising sensor may be selected in accordance with the gaseous components sought to be detected in the embodiment of the present invention.

In an embodiment of the present invention where the electrochemical sensor 150 may comprise three electrodes, the three electrodes may be configured as a working electrode 153*a*, a counter electrode 153*b*, and a reference electrode 153*c*. In operation of one embodiment of the present invention, while the electrochemical sensor 150 is exposed to the gaseous components in the detection/analysis volume 149, suitable electronic measurement equipment may be used to apply a cyclically varying potential between the working electrode 153*a* and the reference electrode 153*c*, and the oxidation current flowing between the working electrode 153*a* and the counter electrode 153*c* may be detected/measured.

In certain aspects of the present invention, the nonsolid conducting material may be in a gelatinous form or non-liquid form and, as such, the gas permeable membrane 143 may not be used. In such aspects, the nonsolid conducting material may itself be used to act as a gas permeable membrane. In such aspects, the gaseous components may diffuse out of the sample in the sample volume 147 and into the gelatinous/non-liquid form nonsolid conducting material. In some aspects, the plurality of the electrodes of the electrochemical sensor 150 may be deposited, for example by screen printing, on a plastic substrate or the like. In further aspects, the electrodes of the electrochemical sensor 150 may be covered with one or more protective membranes to protect them from contamination by contaminants or the like. In such aspects, the one or more membranes may be selected to provide that they allow the gaseous components desired to be detected to pass through the one or more membranes and come into contact with the electrodes.

In certain embodiments of the present invention, one or more of the electrodes of the electrochemical sensor 150 may be configured as an EPPG electrode, a carbon nanotube electrode, an n-doped nanotube electrode, a p-doped nanotube electrode or the like. In certain embodiments of the present invention configured for detection of $H_2S$, one or more of the electrodes may be a boron-doped-diamond electrode, EPPG electrode, a carbon nanotube electrode, an n-doped nanotube electrode, a p-doped nanotube electrode or the like. In particular aspects, the working electrode 150*a* may be configured as a boron-doped-diamond electrode. The reference electrode may be a silver-silver chloride electrode. In embodiments of the present invention configured for detection of $H_2S$, the nonsolid conducting material may be configured as a pH buffered solution.

In embodiments of the present invention configured for detection of lighter hydrocarbons, one or more of the electrodes may be a platinum electrode. In embodiments of the present invention configured for detection of sulphide, one or more of the electrodes may be a gold electrode. In embodiments of the present invention configured for detection of lighter hydrocarbons, one or more of the electrodes may be a palladium electrode. In embodiments of the present invention configured for detection of hydrogen, one or more of the electrodes may be a platinum or palladium electrode. The composition of each of the plurality of electrodes of the electrochemical sensor 150 and/or the nonsolid conducting material may be determined/changed according to the gaseous component or gaseous components for the sampled fluid/mixture sought to be detected/measured. The composition of the working electrode 153*a* may be the variant of most importance with regard to electrode composition selection.

In an embodiment of the present invention, utilizing a potentiostat or similar electronics a voltage sweep may be applied via the electrochemical sensor 150 to the solution in the detection/analysis volume 149, and an electrochemical current may be detected as output. Merely by way of example, upon introduction of $H_2S$ into the detection/analysis volume 149, the voltage sweep may oxidize the $H_2S$ to HS*, and eventually to further products. The current response obtained from such embodiments will be proportional to the concentration of the dissolved sulphide compound. In alternative embodiments, the voltage sweep may provide for reduction of a gas into the detection/analysis volume 149 and a reduction current may be detected and analyzed to determine the presence and/or amount of the gas being reduced. Merely by way of example, a gas such as carbon dioxide may be directly reduced in a system in accordance with an embodiment of the present invention.

In one embodiment of the present invention, electrochemical measurements may be measured using potentiostat or the like comprising a standard three-electrode configuration. A platinum disk may be used as the counter electrode 153b, a silver chloride coated silver disk may be used as the reference electrode 153c and a glassy carbon (GC), boron doped diamond (BDD), basal plane pyrolytic graphite (BPPG) disk, EPPG or a carbon nanotube layer electrode may be used as the working electrode 153a. In embodiments using carbon nanotubes, the carbon nanotubes may be immobilized onto a glassy carbon electrode using dimethylformamide (DMF) as a dispersing agent.

In certain aspects, the nonsolid conducting material may be a pH 7 phosphate buffer or the like. Analysis of the effect of pH on the voltammetric signal at each electrode shows that for $H_2S$ detection according to an embodiment of the present invention, an enhancement in the oxidative current is observed in the presence of sulphide. At each pH value, the oxidation may be more facile at the GC electrode compared to the BDD electrode. Furthermore, increasing the pH of the nonsolid conducting material may provide for shifting an oxidation wave to lower potentials, with more pronounced oxidative waves recorded at the GC electrode, as the pH was increased.

In an embodiment of the present invention, a guard electrode (not shown) may be disposed in the detection/analysis volume 149. The guard electrode may act to scavenge interfering gases from the detection/analysis volume 149 and may provide for detection of a target gas; one that has been selected to be detected by the sensor. Merely by way of example, the guard electrode may be configured to provide for direct oxidation or reduction of a gas that may interfere with detection of the target gas. In this way, the interfering gas may be scavenged from being detected by the working electrode and may not interfere with sensor detection/measurement of the target gas.

Figure 2:
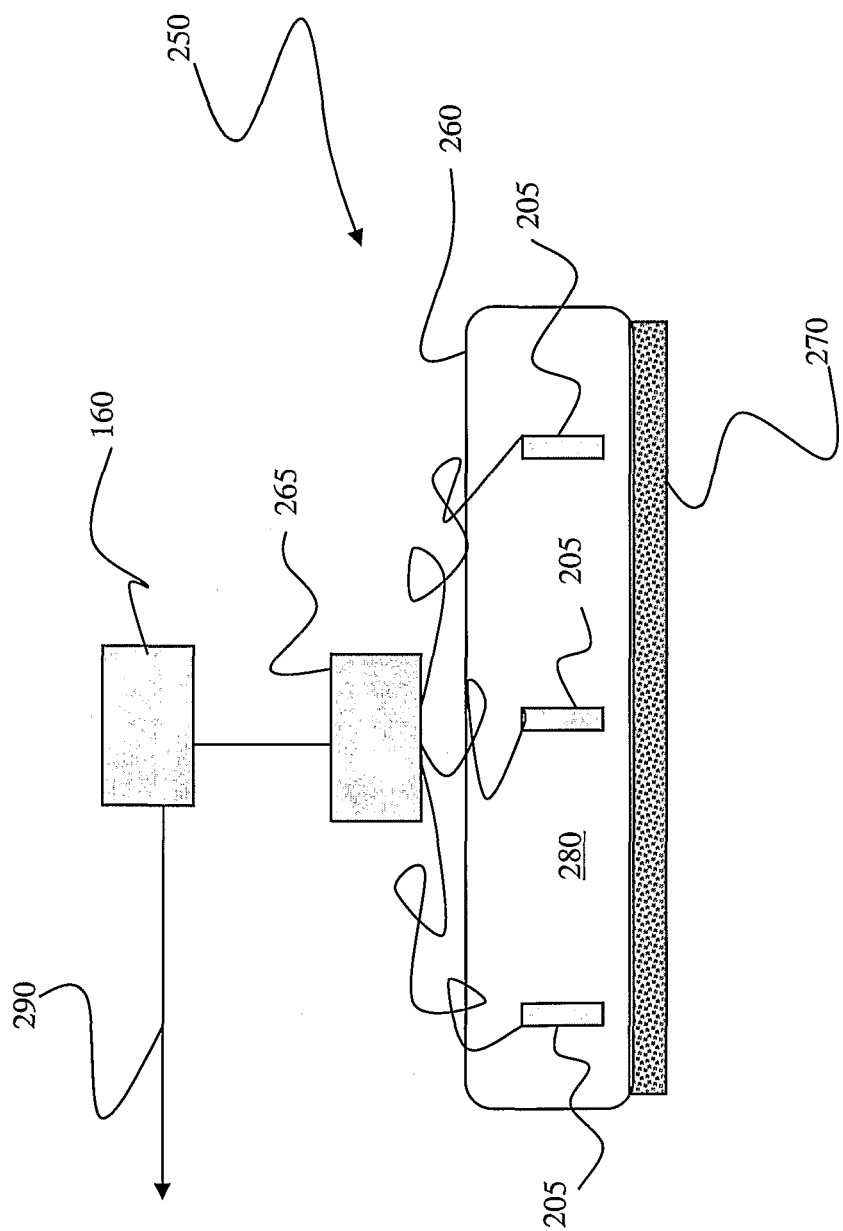
FIG. 2 provides a schematic-type illustration of a gas sensor system for detecting/measuring gaseous components of multiphase mixtures containing one or more hydrocarbons, in accordance with an embodiment of the present invention.

FIG. 2 provides a schematic-type illustration of a gas sensor system for detecting/measuring gaseous components of multiphase mixtures containing one or more hydrocarbons, in accordance with an embodiment of the present invention. In one embodiment of the present invention, a gas sensor 250 may comprise a sensor housing 260. The sensor housing 260 may define an interior volume that may contain a conductive material 280. The conductive material 280 may in many aspects comprise a liquid or a gel.

In an embodiment of the present invention, a plurality of electrodes 205 may be disposed to each be in at least partial contact with the conductive material 280. A potential source 265 may apply a potential difference, potential sweep and/or the like across one or more of the plurality of electrodes 205 and thus create a potential across the conductive material 280. The potential source 265 may be a potentiostat, a galvanostat and/or the like. The current measurement device 160 may be electronically coupled with the potential source 265. In certain aspects, the potential source 265 and the current measurement device 160 may comprise a single device with associated circuitry and be configured to develop a potential across the conductive material 280 and measure any oxidation or reduction current.

In an embodiment of the present invention, the gas sensor 250 may include a gas permeable membrane 270. The gas permeable membrane 270 may be configured to provide for gaseous communication through the gas permeable membrane 270 to the conductive material 280. In operation, the gas sensor 250 may be disposed in a wellbore, a conduit for transporting hydrocarbons, a sampling conduit associated with a wellbore and/or the like to provide that the gas permeable membrane 270 contacts a mixture in the wellbore, the conduit for transporting hydrocarbons, the sampling conduit associated with the wellbore and/or the like. The gaseous components in the mixture may permeate through the gas permeable membrane 270 into the interior of the gas sensor 250. As such, the gas components may be sensed and/or measured by the gas sensor 250 via the measurement of an oxidation or reduction current resulting from the direct oxidation or reduction of the gas components.

An output 290 from the current measurement device 160 may be processed to provide for detection of a particular gaseous component by the gas sensor 250 and or measurement of an amount of a particular gaseous component detected by the gas sensor 250.

In certain embodiments, the conductive material 280 may be a gel or the like and the gas permeable membrane 270 may not be used in the gas sensor 250. In such embodiments, a contact surface (not shown) of the conductive material 280 may be disposed to contact the mixture flowing in the wellbore, the conduit for transporting hydrocarbons, the sampling conduit associated with the wellbore and/or the like and gaseous components in the mixture may enter the conductive material 280.

The gas sensor 250 according to an embodiment of the present invention may be used in a wellbore to provide for measurement while drilling. The gas sensor 250 may be deployed in a wellbore to measure gas components in mixtures in the wellbore after well servicing fluids have been applied to the wellbore and/or surrounding formation. The gas sensor 250 may be combined with coiled tubing, piping or the like to examine mixtures in the wellbore and or a formation. The gas sensor 250 may be permanently installed in the wellbore for monitoring of the wellbore. In other aspects, the gas sensor 250 may be coupled with a hydrocarbon transportation pipe to monitor gas components of hydrocarbon mixtures flowing in the pipe.

Figure 3B:
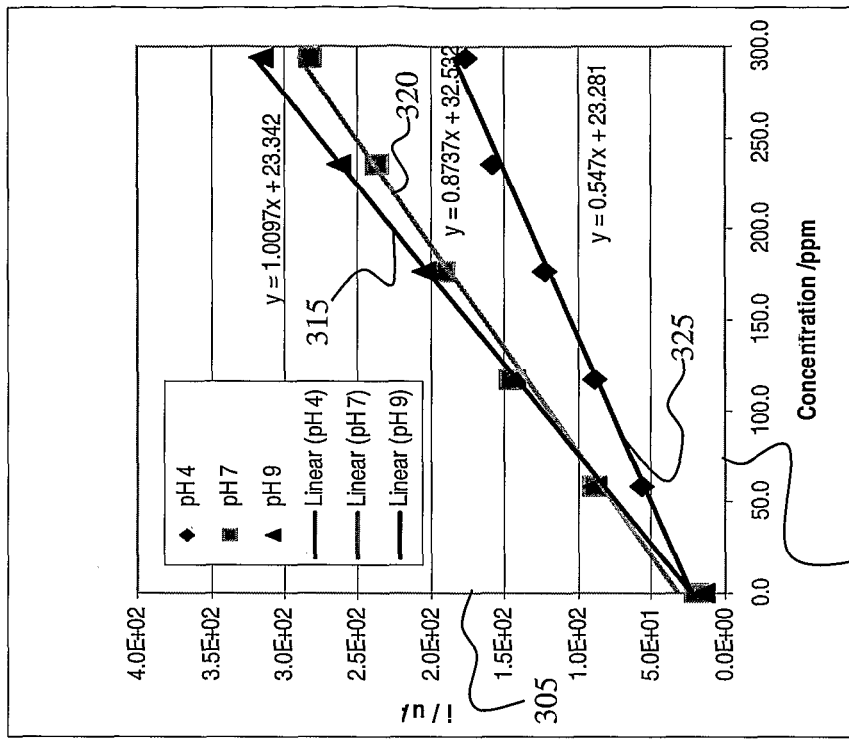
FIG. 3B illustrates oxidation current responses for different sulphide concentrations in different buffer solutions for sulphide detection/measurement systems and methods using a glassy carbon working electrode, in accordance with embodiments of the present invention.
Figure 3A:
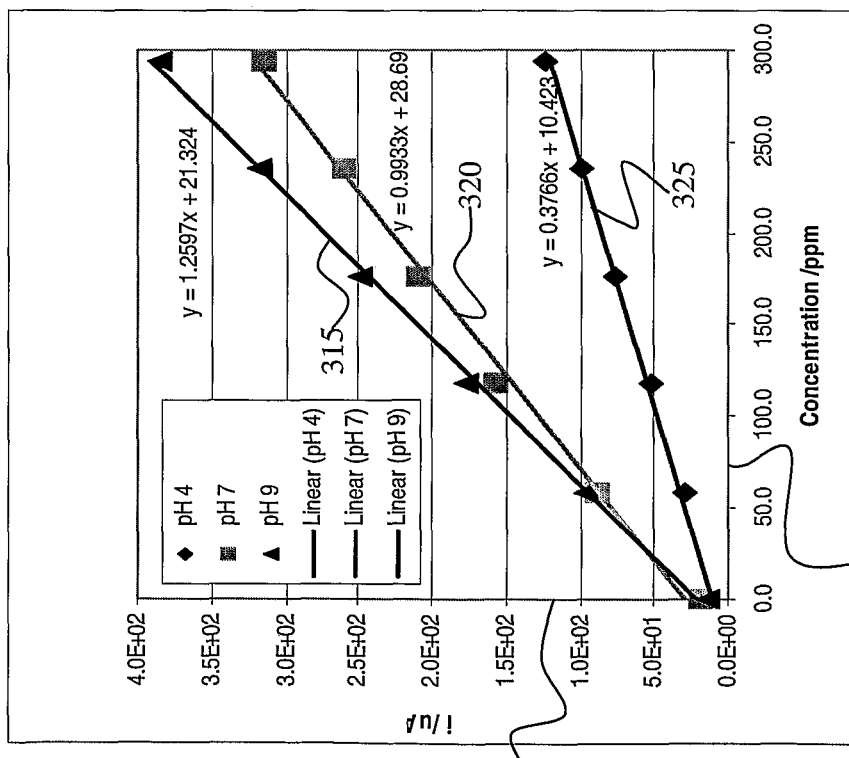
FIG. 3A illustrates oxidation current responses for different sulphide concentrations in different buffer solutions for sulphide detection/measurement systems and methods using a BDD working electrode, in accordance with embodiments of the present invention.

FIGS. 3A and 3B illustrate oxidation current responses for different sulphide concentrations in different buffer solutions for sulphide detection/measurement systems and methods, in accordance with embodiments of the present invention. FIG. 3A illustrates the oxidation current response for different sulphide concentrations in different buffer solutions for a BDD working electrode. FIG. 3B illustrates the oxidation current response for different sulphide concentrations in different buffer solutions for a glassy carbon working electrode.

In FIGS. 3A and 3B, an oxidative current 305 is plotted as a function of a concentration of sulphide 310 for a variety of pH values of the nonsolid conducting material. In FIGS. 3A and 3B, a first plot 315 represents the oxidation current versus sulphide concentration for a pH of 9, a second plot 320 represents the oxidation current versus sulphide concentration for a pH of 7, and a third plot 325 represents the oxidation current versus sulphide concentration for a pH of 4. The figures show that increasing the pH may enhance the analytical signal produced by a system in accordance with an embodiment of the present invention. As such, in certain aspects, high pH solutions may be used as the nonsolid conducting material.

In order for the H$_2$S to be oxidized in a system in accordance with the present invention, the H$_2$S may as an initial matter go through a one electron transfer step whilst losing a single proton, prior to further reactions, as outlined below:

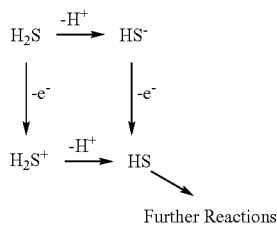

This so called 'scheme of squares' shows that there are two reaction pathways in which the H$_2$S may be oxidized to HS, and therefore either the loss of the electron or loss of the proton will be rate-determining. The results in FIGS. 3A and 3B show only a slight increase in the oxidative current at pH 4.0 when H$_2$S was introduced to the system. At this pH over 99% of the dissolved sulphide will be H$_2$S and therefore may be difficult to oxidise. By increasing the pH, the analytical signal in an embodiment of the present invention may be enhanced. Similarly, for other gaseous components of the wellbore fluid, formation fluid and/or the like to be tested for by an embodiment of the present invention, of the pH of a buffering solution and/or nonsolid conducting material may provide for an enhanced oxidation current that may be used for detecting and/or measuring the gaseous component of interest. While increasing pH values above 5 may increase the detection/measuring signal for H$_2$S, for other gases reducing pH values below 5 may provide the same effect.

In certain aspects of the present invention, a basal plane pyrollytic graphite (BPPG) electrode may be used as the working electrode and a direct oxidation current may be used to detect/measure sulphides in a sample of the wellbore fluids, formation fluids and/or the like. Merely by way of example, a phosphate buffer with a pH around 6.9 may be used as the nonsolid conducting material.

In other aspects of the present invention, a carbon nanotube layer may be provided on the working electrode and may provide for detection/measuring of various gaseous components. Again, merely by way of example, the working electrode with the carbon nanotube layer may be used with a phosphate buffer solution with a pH around 7 to provide for the detection/measurement of the gaseous components of the wellbore fluids, formation fluids and/or the like. In yet other aspects, the working electrode may be an edge plane pyrollytic graphite (EPPG) electrode and may be used with a buffer solution to provide for detection/measurement of gaseous components of formation and/or wellbore fluids using direct oxidation, in accordance with an embodiment of the present invention.

Figure 4:
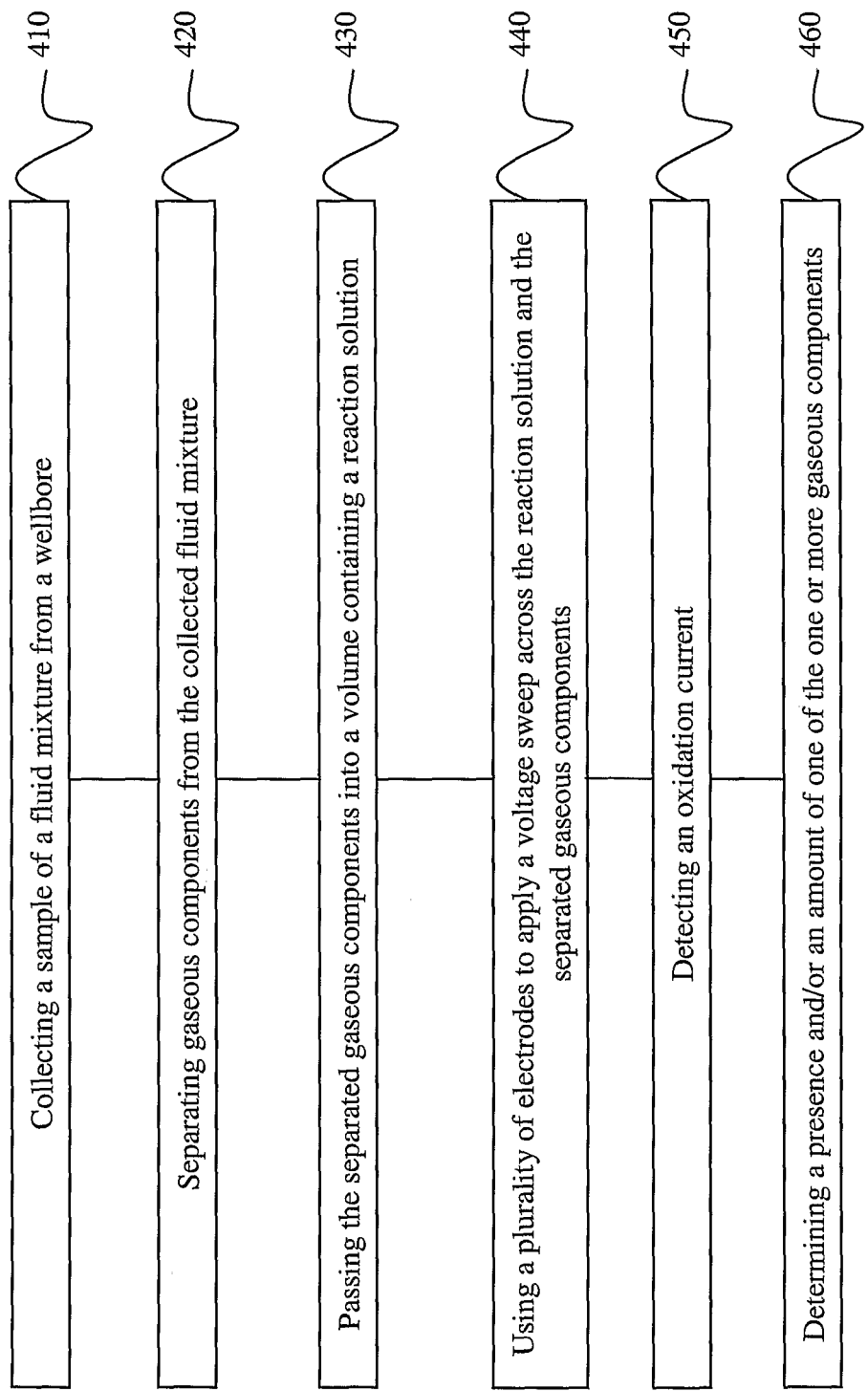
FIG. 4 is a flow-type representation of a process for detecting/measuring gaseous components of downhole fluids in a wellbore, in accordance with an embodiment of the present invention.

FIG. 4 is a flow-type representation of a process for detecting/measuring gaseous components of downhole fluids, in accordance with an embodiment of the present invention. In step 410, a sample of a fluid mixture may be collected from a wellbore. A wellbore tool may be positioned in the wellbore and may collect a sample of a wellbore fluid, a formation fluid from outside the wellbore or the like. The sample may be collected by means of a probe and pump assembly or the like. For formation fluid acquisition a guarded probe may be utilized to provide for separation of the formation fluid from wellbore fluids to provide for a clean sample.

In step 420, gaseous components of the collected fluid sample may be separated from the rest of the fluid sample. A gas permeable membrane or the like may be used to provide for the separation of the gaseous component of the sample from the remaining fluid sample. In other aspects, a gel or the like may be used to create a gas permeable barrier.

In step 430, the separated gaseous components may flow into a volume containing a nonsolid conducting material. In some embodiments of the present invention, the nonsolid conducting material may be a buffer solution. In certain aspects the nonsolid conducting material may have a high pH value. In alternative aspects, the nonsolid conducting material may have a low pH value. In step 440, a plurality of electrodes may be configured to provide for contact between the plurality of the electrodes and the nonsolid conducting material. In some embodiments of the present invention, the plurality of electrodes may comprise a working electrode, a reference electrode and a counter electrode. The plurality of the electrodes may be used to apply a voltage, a voltage sweep or the like to the nonsolid conducting material and the separated gaseous components in the volume. The composition/characteristics of the nonsolid conducting material and/or one or more of the plurality of electrodes may be selected to provide for detection/measurement of a desired gaseous component. For example, a platinum working electrode may be used to provide for detection of methane.

In step 450, an oxidation current may be detected and/or measured. The oxidation current being detected/measured resulting from direct oxidation of one or more of the gaseous components in the volume, wherein the one or more gaseous components in the volume are oxidized by the voltage applied by the plurality of the electrodes. In step 460, the oxidation current may be processed to provide for detection and/or measuring an amount of one of the gaseous components in the volume.

In the foregoing description, for the purposes of illustration, various methods and/or procedures were described in a particular order. It should be appreciated that in alternate embodiments, the methods and/or procedures may be performed in an order different than that described. It should also be appreciated that the methods described above may be performed by hardware components and/or may be embodied in sequences of machine-executable instructions, which may be used to cause a machine, such as a general-purpose or special-purpose processor or logic circuits programmed with the instructions, to perform the methods. These machine-executable instructions may be stored on one or more machine readable media, such as CD-ROMs or other type of optical disks, floppy diskettes, ROMs, RAMs, EPROMs, EEPROMs, magnetic or optical cards, flash memory, or other types of machine-readable media suitable for storing electronic instructions. Merely by way of example, some embodiments of the invention provide software programs, which may be executed on one or more computers, for performing the methods and/or procedures described above. In particular embodiments, for example, there may be a plurality of software components configured to execute on various hardware devices. Alternatively, the methods may be performed by a combination of hardware and software.

What is claimed is:

1. A method for downhole analysis of a fluid sample in a wellbore, comprising:
    collecting a sample of a fluid mixture at a downhole location;
    separating a hydrogen sulphide gas component from the sample of the fluid mixture and dissolving the separated gas component in a pH buffered nonsolid conductive material;
    providing a plurality of electrodes in contact with the nonsolid conductive material;
    using the plurality of electrodes to apply a potential across the conductive material and thereby directly oxidize or reduce the hydrogen sulphide gas component separated from the sample of the fluid mixture;
    measuring current flowing through the conductive material resulting from the direct oxidization or reduction of the hydrogen sulphide gas component; and
    determining a presence of the hydrogen sulphide gas component or an amount of the hydrogen sulphide gas component from the measured current.

2. The method of claim 1, wherein the sample of the fluid mixture is collected from a formation surrounding the wellbore.

3. The method of claim 1, wherein the step of separating a gas component from the sample of the fluid mixture comprises contacting the sample of the fluid mixture with a gas permeable membrane.

4. The method of claim 1, wherein one of the plurality of electrodes comprises a working electrode and the working electrode comprises one of gold, palladium, EPPG, carbon nanotubes, n-doped nanotubes and p-doped nanotubes.

5. The method of claim 1, wherein one of the plurality of electrodes comprises a working electrode and the working electrode comprises an EPPG electrode.

6. The method of claim 1, wherein one of the plurality of electrodes comprises a working electrode and the working electrode has n-doped nanotubes or carbon nanotubes disposed on an outer surface of the working electrode.

7. The method of claim 1, wherein a gas sensor configured to collect the sample of a fluid mixture, separate the hydrogen sulphide gas component from the sample of the fluid mixture and dissolve the separated gas component in a pH buffered nonsolid conductive material in contact with the plurality of electrodes is coupled with a logging tool and is configured to determine a presence of or measure the hydrogen sulphide gas component in the logging tool.

8. The method of claim 1, wherein a gas sensor configured to collect the sample of a fluid mixture, separate the hydrogen sulphide gas component from the sample of the fluid mixture and dissolve the separated gas component in a pH buffered nonsolid conductive material in contact with the plurality of electrodes is coupled with a coiled tubing system and is configured to determine a presence of or measure the hydrogen sulphide gas component in a sample of a mixture flowing in the coiled tubing.

9. The method of claim 1, wherein the nonsolid conductive material comprises a liquid or a gel buffered to a pH greater than 5.

10. The method of claim 1, wherein the nonsolid conductive material is buffered to a pH of at least 6.9.

11. The method of claim 1, wherein the plurality of electrodes comprises a working electrode which is a carbon electrode, a counter electrode and a reference electrode.

12. A method for downhole analysis of a fluid in a subsea pipeline for transporting hydrocarbons comprising:
    collecting a sample of a fluid mixture from the pipeline;
    separating a hydrogen sulphide gas component from the sample of the fluid mixture and dissolving the separated gas component in a pH buffered nonsolid conductive material;
    providing a plurality of electrodes in contact with the nonsolid conductive material;
    using the plurality of electrodes to apply a potential across the conductive material and thereby directly oxidize or reduce the hydrogen sulphide gas component separated from the sample of the fluid mixture;
    measuring current flowing through the conductive material resulting from the direct oxidization or reduction of the hydrogen sulphide gas component; and
    determining a presence of the hydrogen sulphide gas component or an amount of the hydrogen sulphide gas component from the measured current.

* * * * *